United States Patent

Nambu et al.

[11] Patent Number: 4,881,251
[45] Date of Patent: Nov. 14, 1989

[54] COMPUTED TOMOGRAPH APPARATUS

[75] Inventors: Kyojiro Nambu; Toshihiro Rifu, both of Tochigi, Japan

[73] Assignee: Kabushiki Kaisha Toshiba, Kawasaki, Japan

[21] Appl. No.: 78,969

[22] Filed: Jul. 29, 1987

[30] Foreign Application Priority Data

| Jul. 31, 1986 | [JP] | Japan | 61-181061 |
| Aug. 5, 1986 | [JP] | Japan | 61-182650 |
| Aug. 5, 1986 | [JP] | Japan | 61-182651 |
| Aug. 19, 1986 | [JP] | Japan | 61-192015 |

[51] Int. Cl.$^4$ .............................................. A61B 6/02
[52] U.S. Cl. .................................. 378/7; 378/86; 378/87; 378/4
[58] Field of Search ............... 378/4, 7, 19, 86–89; 250/370.09

[56] References Cited

U.S. PATENT DOCUMENTS

| 3,769,507 | 10/1973 | Kenney et al. | 378/86 |
| 3,937,965 | 2/1976 | Vasseur | 378/7 |
| 4,055,767 | 10/1977 | Allemand | 378/19 |
| 4,123,654 | 10/1978 | Reiss et al. | 378/87 |
| 4,149,080 | 4/1979 | Schittenhelm | 378/7 |
| 4,187,427 | 2/1980 | Lusano | 378/19 |
| 4,286,156 | 8/1981 | Wagner | 378/7 |
| 4,292,538 | 9/1981 | Carlson | 378/19 |
| 4,709,382 | 11/1987 | Sones | 378/5 |
| 4,725,734 | 2/1988 | Nishiki | 378/19 |

Primary Examiner—Carolyn E. Fields
Assistant Examiner—Joseph A. Hynds
Attorney, Agent, or Firm—Finnegan, Henderson, Farabow, Garrett and Dunner

[57] ABSTRACT

A computed tomograph apparatus for obtaining tomograms of a subject under examination comprises a supporting table for supporting the subject, and on which a tomogram image pick-up area is defined. The apparatus further comprises an X-ray source for radiating X-rays onto the image pick-up area. X-rays emitted from the X-ray source proceed along a slice plane intersecting with the image pick-up area. A principal detector is provided within the slice plane, and detects X-rays transmitted linearly.

17 Claims, 12 Drawing Sheets

COMPUTED TOMOGRAPH APPARATUS

BACKGROUND OF THE INVENTION

The present invention relates to a computed tomograph apparatus used for obtaining tomograms of subjects, for the purpose of medical examination.

Figure 1:
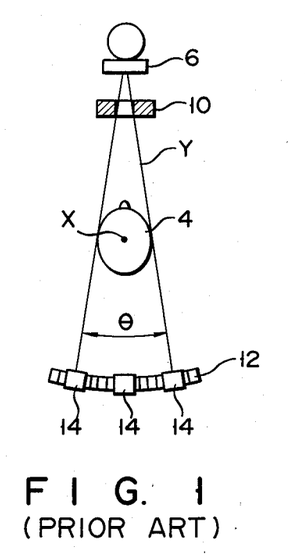
FIG. 1 is a schematic view of a computer tomograph apparatus according to the prior art.
Figure 2:
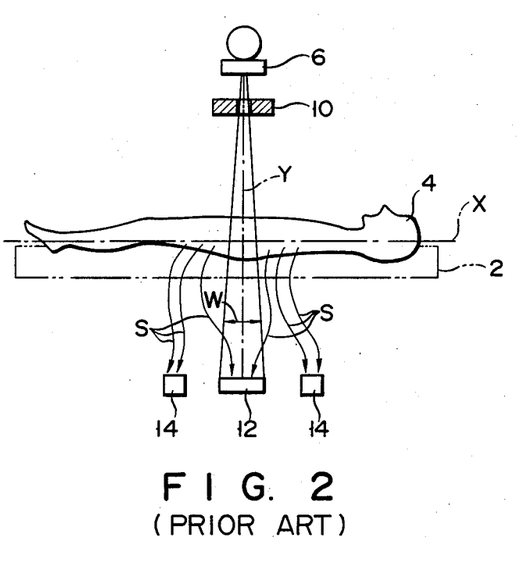
FIG. 2 is a side view of the apparatus of FIG. 1.

FIGS. 1 and 2 schematically illustrate a conventional computed tomograph apparatus. In this apparatus, subject 4 is laid on bed 2. An X-ray tube 6 for emitting X-rays is located above bed 2, for emitting X-rays onto subject 4. The X-rays emitted from tube 6 proceed as a flux of rays along slice plane Y which is perpendicular to the surface of bed 2. More specifically, the radiated X-rays are converted, by collimator 10, to a fan-shaped beam having a sector angle $\theta$ and a slice thickness W. A principal detector 12, for detecting principal X-rays transmitted linearly through subject 4, and a number of scattered ray detectors 14, for detecting scattered X-rays other than the principal X rays, are arranged opposite to X-ray tube 6, as viewed from subject 4 on bed 2. Principal detector 12 comprises a plurality of channels and is located within the fan-shaped beam. Each of the scattered ray detectors 14 comprises a single channel and is located off the path of the beam and situated symmetrically with respect to slice plane Y. Principal detector 12 and each of scattered ray detectors 14 include a scintillation detector which consists of, for example, a scintillator and photodiodes. As X-ray tube 6, collimator 10, principal detector 12, and scattered ray detector 14 rotate integrally around axis X of rotation, with X-ray tube 6 continuously irradiating subject 4 with X-rays, a tomogram of subject 4 is gradually formed.

When forming a tomogram, preferably only the X-rays emitted from X-ray tube 6 and linearly transmitted through subject 4, and which are eventually detected by principal detector 12, should be used to produce a tomogram image, after processing the data representing the absorbed doses of the X-rays.

However, the X-rays which enter principal detector 12 contain not only those transmitted though subject 4, but also some which are scattered within the subject and others which are not transmitted though the subject at all, arriving at detector 12 simply by bypassing the subject (these rays are hereinafter referred to as scattered rays S). Therefore, it is necessary to include compensatory measures in the computer processing, so as to ensure generation of an accurate tomogram image, taking into account the presence of such scattered rays S. Accordingly, a number of scattered ray detectors 14 are provided in the vicinity of principal detector 12. Since the scattered ray detectors 14 are located off the path of the X-ray beam having a slice thickness W, they do not receive any incident principal X-rays, their incident rays being limited only to scattered rays.

For the above mentioned compensatory measures to be effective, however, it is necessary that rays S scattered in the same area of subject 4 are detected not only by any of scattered ray detectors 14 but also by principal detector 12, because if such rays S are detected only by scattered ray detectors 14, a correct compensatory measures cannot be achieved, thereby permitting artifacts to appear in the resulting tomogram image.

In a computed tomograph apparatus according to the prior art, while a principal detector 12 and scattered ray detectors 14 are provided in the vicinity of each other, their positional relationship is not specifically defined. This is because no definite relationship can be established between the scattered rays incident to principal detector 12 and those incident to scattered ray detectors 14. Consequently, the compensatory measures cannot be correctly achieved.

SUMMARY OF THE INVENTION

It is therefore the object of the present invention to provide a computed tomograph apparatus which permits proper and correct compensations to be made for scattered X-rays.

According to an aspect of the present invention, there is provided a computed tomograph apparatus for obtaining tomograms of a subject under examination, which comprises a supporting table for supporting said subject, and on which a tomogram image pick-up area is defined, an X-ray source for radiating X-rays onto said image pick-up area, X-rays proceeding along a slice plane which intersects with said image pick-up area, a principal detector provided in said slice plane, for detecting X-rays transmitted linearly through said subject placed in said image pick-up area, and a scattered ray detector provided in an arc existing in a plane perpendicular to said slice plane, for detecting X-rays other than those transmitted linearly through said subject, said arc having its center in said slice plane and a radius which is equal to the distance between said center and said principal detector.

With a computed tomograph apparatus constructed thus, since the principal detector and the scattered ray detector are located at the same distance from the area where scattered rays are most apt to occur, a mathematical relationship can be established between the scattered rays incident on the principal detector and those incident on the scattered ray detectors. Hence, the scattered rays can be properly and correctly compensated in accordance with this relationship.

DETAILED DESCRIPTION OF THE PREFERRED EMBODIMENTS

Figure 3:
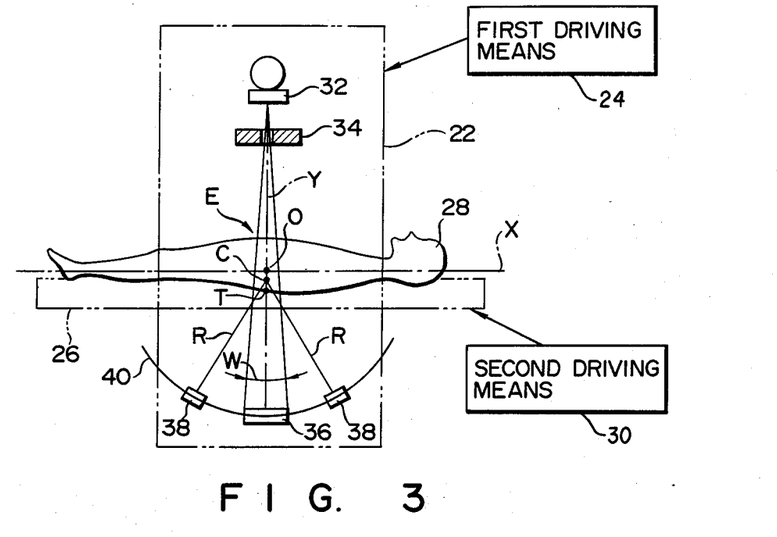
FIG. 3 is a schematic view illustrating a first embodiment of the computed tomograph apparatus according to the present invention.

FIG. 3 schematically illustrates a first embodiment of the present invention. As is shown in this figure, a ring-shaped scanner body 22 is rotated around the axis X of rotation by first driving means 24. A subject 28 of examination is laid on bed 26, above which tomogram image pick-up area E is defined for subject 28. Bed 26 can be moved along the axis X of rotation by second driving means 30, within the operational space of scanner body 22.

X-ray tube 32, collimator 34, principal detector 36, and scattered ray detectors 38 are incorporated in scanner body 22. X-ray tube 32 irradiates subject 28 laid on bed 26 with X-rays. The X-rays proceed along slice plane Y which is perpendicular to the axis X of rotation. In other words, the radiated X-rays are converted into a fan-shaped slice of a beam having a sector angle $\theta$ and a slice thickness W. The principal detectors 36 and the scattered ray detectors 38 are located opposite to X-ray tube 32. Principal detector 36 detects the X-rays (principal rays) which are linearly transmitted through subject 28. Scattered ray detectors 38 detect X-rays (scattered rays) other than those linearly transmitted, for example the X-rays which are scattered by subject 28. Principal detector 36 comprises a plurality of channels and is located within the fan-shaped slice of beam. Each of the scattered ray detectors 38 comprises a single channel and is located off the path of the beam. Detectors 38 are arranged symmetrically with respect to slice plane Y, for example, at each end of the arc of the sector for the path of X-ray beam formed at the opposite side of X-ray tube 32, as viewed from subject 28. Principal detector 36 and each of the scattered ray detectors 38 comprise a scintillation detector which consists of, for example, a scintillator and photodiodes. As X-ray tube 32, collimator 34, principal detector 36 and scattered ray detectors 38 integrally rotate around subject 28, with X-ray tube incessantly irradiating the subject with X-rays, a tomogram of subject 4 is gradually formed.

Said scattered ray detectors 38 are arranged in arc 40 found in a plane perpendicular to slice plane Y.

It should be noted that, if distribution of scattered ray detectors 38 is expressed by u (X, Y, Z), the center of the arc is found on the center of gravity (xg, yg, zg) of the X-ray absorber. Thus, $$Z_y = \int_0^{x_{mzx}} \int_0^{y_{max}} \int_0^{z_{max}} Ze^{-g(x,y,z)} \cdot \mu(x,y,z)dxdydz /$$

$$\int_0^{x_{max}} \int_0^{y_{max}} \int_0^{z_{max}} e^{-g(x,y,z)} \cdot \mu(x,y,z)dxdydz$$

Now, if $$g(x,y,z) = \int_0^z \mu(x,y,t)dt, a(x,y) = \int_0^{z_{max}} e^{-g(x,y,z)}$$

is assumed, then $$Y_g = \int_0^{x_{max}} \int_0^{y_{max}} y \cdot a(x,y)dxdy / \int_0^{x_{max}} \int_0^{y_{max}} a(x,y)dxdy$$

$$X_g = \int_0^{x_{max}} \int_0^{y_{max}} x \cdot a(x,y)dxdy / \int_0^{x_{max}} \int_0^{y_{max}} a(x,y)dxdy$$

Arc 40 has its center C in slice plane Y, and its radius R is equal to the distance between center C and principal detector 36. Center C is within image pick-up area E which is opposite to X-ray tube 32, as viewed from the plane which contains the axis of rotation X and is perpendicular to slice plane Y.

Figure 4:
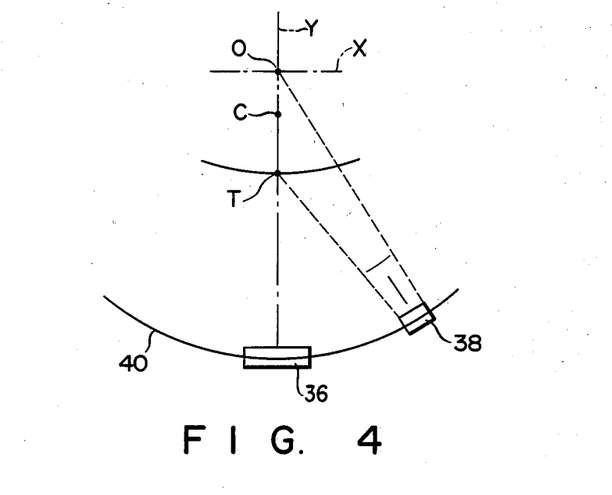
FIG. 4 is a schematic view illustrating the arrangement of a scattered ray detector used in the first embodiment of the present invention.

As shown in FIG. 4, scattered ray detectors 38 are so arranged that their most sensitive directions are found within the area defined by connecting point O of intersection of axis X of rotation and slice plane Y, point T of intersection of plane Y and the outer periphery of the image pick-up area E and the scattered ray detector.

Since ray detectors 38 are each located at the same distance from a spot within slice plane Y, and can generate scattered X-rays most intensively, principal detector 36 and scattered ray detectors 38 respectively have an approximately same amount of incident scattered rays.

Therefore, the relationship between the scattered rays incident of the principal detector 36 and those incident to any of the scattered ray detectors 38 can be mathematically defined, and the resulting tomogram image pick-up can be correctly compensated.

Figure 5:
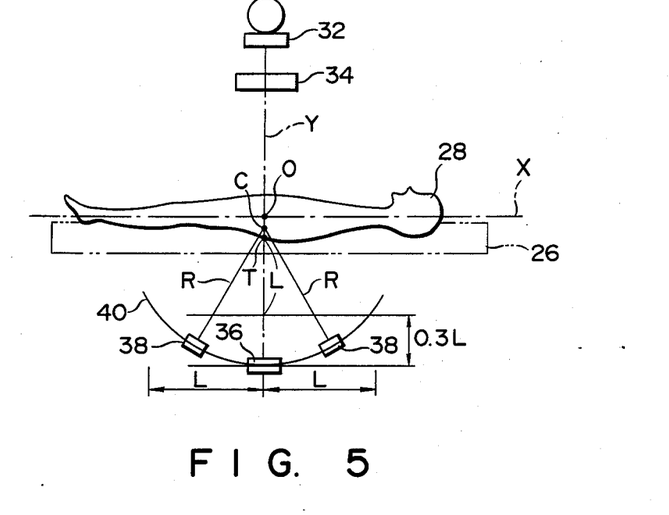
FIG. 5 is a side view of a first modification of the first embodiment shown in FIG. 3.

FIG. 5 illustrates a modification of the apparatus shown in FIG. 3. In this modified embodiment, scattered ray detectors 38 are provided within a specific area. Point T of intersection is at distance L from principal detector 36. Each of scattered ray detectors 38 is located at distance L from slice plane Y, while it is found within 0.3L from the line which is parallel to axis X of rotation and passes principal detector 36 toward axis X.

With this modified embodiment, the effect of scattered rays can be more accurately compensated than in the case of the original, although both are functionally identical.

Figure 6:
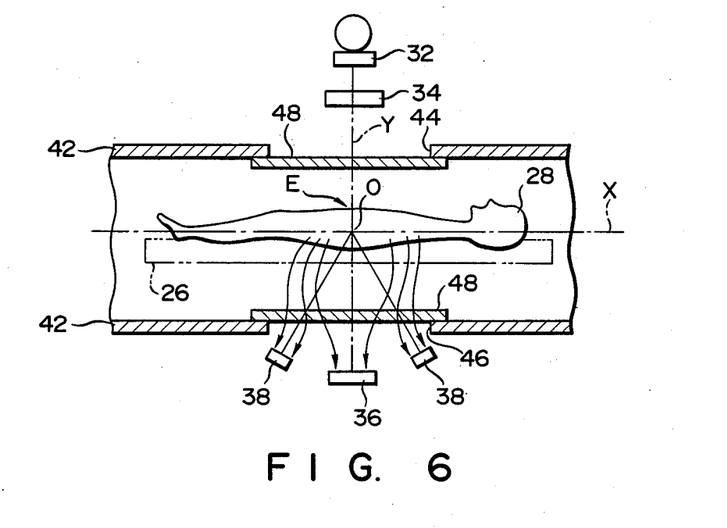
FIG. 6 is a sectional side view of a second modification of the first embodiment shown in FIG. 3.

FIG. 6 shows another modification of the apparatus shown in FIG. 3. In this modified embodiment, protective housing 42 is provided between X-ray tube 32, on the one hand, and principal detector 36 and scattered ray detectors 38, on the other, to protect the subject 28 by defining the image pick-up area E. Protective housing 42 is made of a thick walls that absorbs X-rays at a relatively high rate. Housing 42 has a first opening 44 to admit X-rays emitted by X-ray tube 32 into the image pick-up area E, and a second opening 46 to admit the linearly transmitted X-rays (principal rays) coming though subject 28, laid in the image pickup area E, into principal detector 36, and the rest of the rays (scattered rays) into scattered ray detectors 38.

The computed tomograph apparatus shown in FIG. 6 can be as effective as the above examples, because the scattered rays generated in subject of examination 28, as well as those generated within protective housing 42, are incident on all the detectors 36 and 38 at an approximately similar rate.

Figure 7:
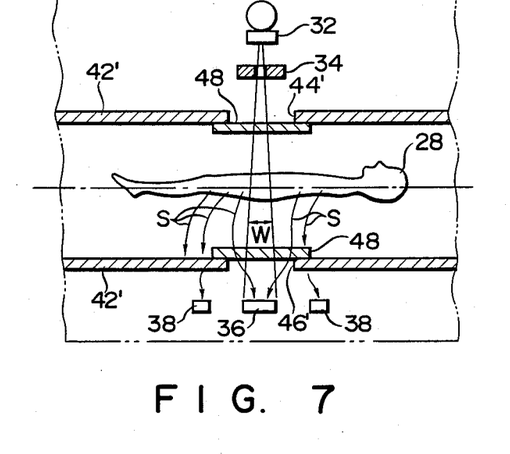
FIG. 7 is a side view illustrating an alternative profile of the second modification shown in FIG. 7.

FIG. 7 is an alternative of the above described second modified embodiment. In this example, the area of opening 44' and that of opening 46' are such that the required minimum amount of principal X-rays of the slice of beam with thickness W can pass through them after emitted from X-ray tube 32. Scattered ray detectors 38 can receive only those scattered X-rays S that are generated within subject 28 and then transmitted through protective housing 42. On the other hand, principal detector 36 receives most of the scattered rays that are transmitted through cover 48. As a result, this configuration can give rise to a distorted relationship between the amount of scattered rays incident on principal detector 36 and the amount of rays incident on scattered ray detector 38, leading to an incorrect compensation.

Figure 8:
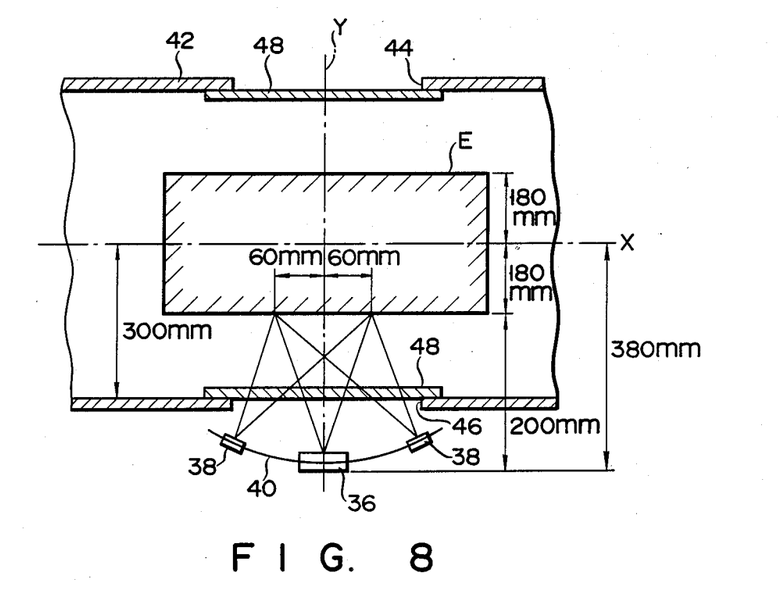
FIG. 8 is a sectional side view of a third modification of the first embodiment shown in FIG. 3.

FIG. 8 shows a third modification of the first embodiment shown in FIG. 3. In this modified embodiment, the image pick-up area is cylindrical, with some critical dimensions as shown in the illustration. The cylindrical image pick-up area E has a radius of 180 mm, scattered rays being assumed to be generated within 60 mm from slice plane Y to both the left and the right inside the pick-up area. The size of the opening 46 is so determined that scattered rays which are generated at a point 60 mm away from slice plane Y and proceed linearly toward principal detector 36, and scattered rays can pass through it without being obstructed. The arrangement of this modified embodiment has a similar effect as the original.

In the first embodiment, scattered ray detectors 38 are provided at both sides of principal detector 36. They can also be placed at only one side of principal detector 36.

Figure 9:
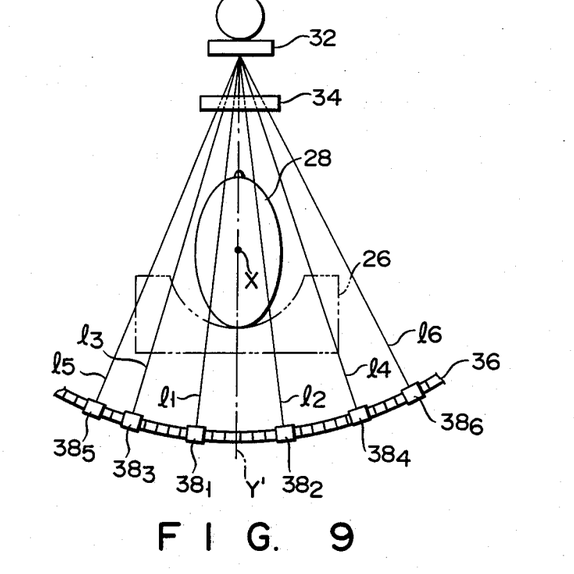
FIG. 9 is a front view of a second embodiment of the computed tomograph apparatus according to the present invention.
Figure 10:
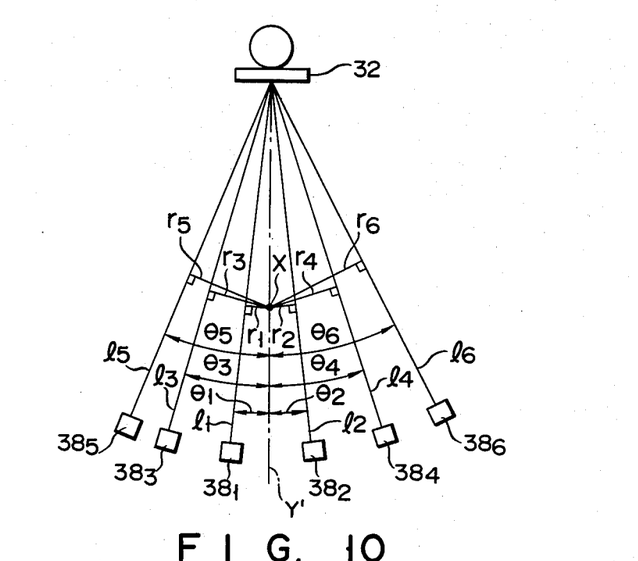
FIG. 10 is a front view of the apparatus shown in FIG. 9, illustrating the arrangement of the scattered ray detectors.

FIG. 9 shows a second embodiment of the present invention. In this embodiment, a plurality of scattered ray detectors $38_1$-$38_6$ are provided asymmetrically on both sides of the plane Y' containing X-ray tube 32 and the axis of rotation X. When lines $l_1$~$l_6$ are drawn, connecting scattered ray detectors $38_1$-$38_6$ to X-ray tube 32, and the angles formed by the lines $l_1$~$l_6$ and the center line Y' are denoted by $\theta_1$-$\theta_6$ as shown in FIG. 10. Their mutual relationships can be expressed as follows:

$$\theta_1 < \theta_2 < \theta_3 < \theta_4 < \theta_5 < \theta_6.$$

In other words, if a perpendicular line is drawn from the intersection of slice plane Y and axis X of rotation down to each of the lines $l_1$~$l_6$, and the lengths of the perpendiculars are respectively denoted by $r_1$-$r_6$, then their mutual relationships can be given as follows:

$$r_1 < r_2 < r_3 < r_4 < r_5 < r_6.$$

Figure 11:
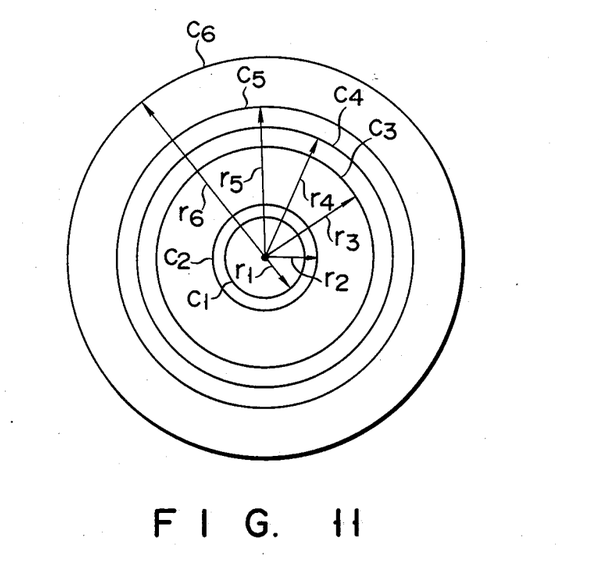
FIG. 11 is a schematic illustration of the function of the scattered ray detector arranged as is shown in FIG. 10.

Now, as shown in FIG. 11, if X-ray tube 32, principal detector 36 and scattered ray detectors $38_1$-$36_6$ are integrally rotated around the axis of rotation X for scanning, lines $l_1$~$l_6$ are moved and circumscribed with six different circles $C_1$-$C_6$ having respectively radius $r_1$-$r_6$. The number of circles $C_1$-$C_6$ is equal to that of scattered ray detectors $38_1$-$38_6$.

Figure 12:
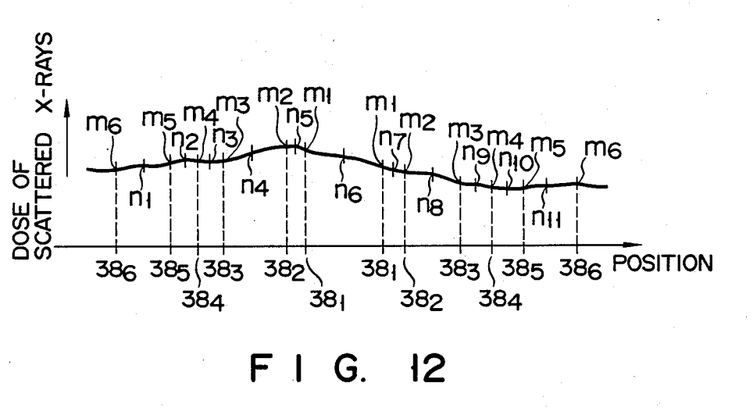
FIG. 12 is a graphical illustration of the characteristics of the scattered ray detectors arranged as is shown in FIG. 10.

FIG. 12 is a graphical illustration of the doses of scattered X-rays measured by detectors $38_1$-$38_6$ in an experiment. Values $m_1$-$m_6$ for respective detectors $38_1$-$38_6$ have been actually recorded by the detectors in one measurement, proving that the level of accuracy of the measurement is considerably high. The values $n_1$-$n_6$ are interpolated dose values for positions between scattered ray detectors $38_1$-$38_6$. It will be appreciated that the accuracy of the interpolations is high because there exist circles $C_1$-$C_6$ whose number corresponds to the number of scattered ray detectors $38_1$-$38_6$, and the distance between any two adjacent circles is relatively short. This means that detected errors have small discrepancies, and measured values can be correctly compensated to eliminate any artifacts to be involved. Moreover, by appropriately arranging the scattered ray detectors $38_1$-$38_6$ or by appropriately positioning the subject of examination, the effects of artifacts may be offset by one another.

Figure 13:
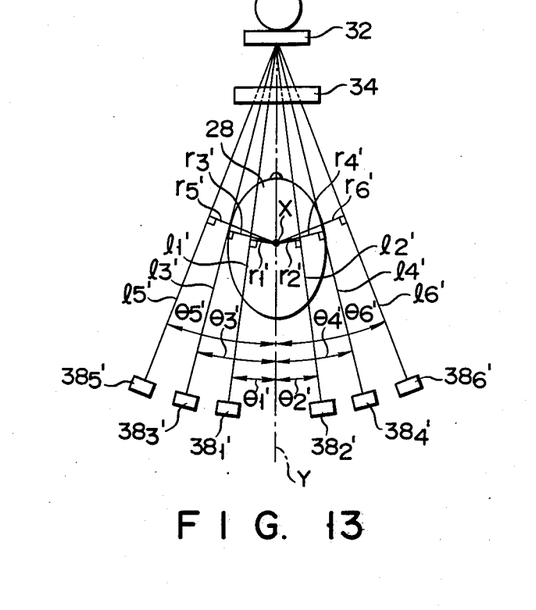
FIG. 13 is a schematic illustration of an alternative arrangement of the scattered ray detectors shown in FIG. 10.

FIG. 13 illustrates an alternative arrangement of the scattered ray detectors, presented for comparison with the second embodiment. In this case, scattered ray detectors $38_1'$-$38_6'$ are located symmetrically to the fan-shaped slice of beam path containing X-ray tube 32 and the axis X of rotation. In other words, if lines $l_1'$-$l_6'$ are drawn, connecting X-ray tube 32 to scattered ray detectors $38_1'$-$38_6'$, and the angles formed respectively by lines $l_1'$-$l_6'$ and the surface of the slice of beam are denoted as shown in FIG. 13, then the mutual relationship of the angles can be expressed as follows;

$$\theta_1' = \theta_2' < \theta_3' = \theta_4' < \theta_5' = \theta_6'$$

Or, if perpendiculars are respectively drawn from the point of intersection of axis X of rotation and the center line of slice Y to lines $l_1'$~$l_6'$, their mutual relationship can be given;

$$r_1' = r_2' < r_3' = r_4' < r_5' = r_6'$$

Figure 14:
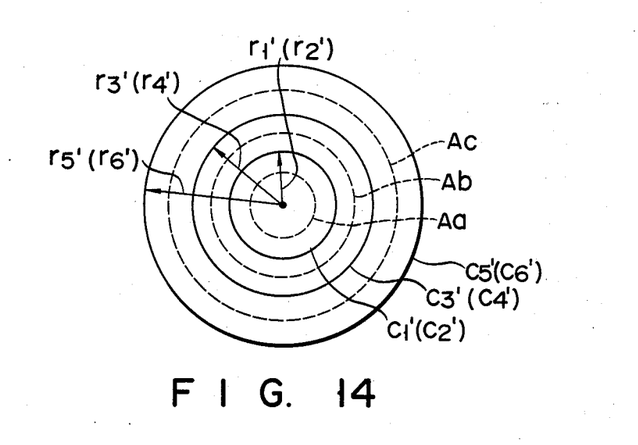
FIG. 14 is a schematic illustration of the function of the scattered ray detectors arranged as is shown in FIG. 13.

When X-ray tube 32, principal detector 36 and scattered ray detectors $38_1'$–$38_6'$ are integrally rotated around the axis of rotation X for scanning, as shown in FIG. 14, lines $L_1$–$L_6$ move and are circumscribed by three different circles $C_1'$ ($C_2'$), $C_3'$ ($C_4'$) and $C_5'$ ($C_6'$) having diameters $r_1'$ (=$r_2'$), $r_3'$(=$r_4'$) and $r_5'$ (=$r_6'$). Obviously, the number of effective circles in this example is half the number of scattered ray detectors $38_1'$–$38_6'$.

Figure 15:
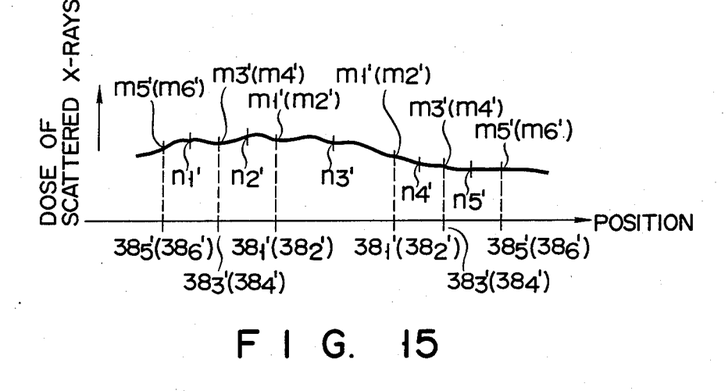
FIG. 15 is a graphical illustration of the characteristics of the scattered ray detectors arranged as is shown in FIG. 13.

FIG. 15 shows an example of distribution of the scattered ray doses detected by detectors $38_1'$–$38_6'$. These doses have been actually measured by the respective detectors. An enhanced accuracy level of measurement may be realized by the apparatus of this example as compared with any conventional apparatus of this type. Nonetheless, the level of accuracy cannot be as high as that realized by the second embodiment as described earlier, because $m_1' = m_2'$, $m_3' = m_4'$ and $m_5' = m_6'$, and only half as many effective measurements is realized in this apparatus. In other words, since the distance separating circles $C_1'$ ($C_2'$), $C_3'$ ($C_4'$) and $C_5'$ ($C_6'$) from one another are longer than those of the second embodiment, interpolated values $n_1'$–$n_5'$ are inevitably less reliable than their counterparts in the second embodiment. This means that there may be relatively great discrepancies among errors of measurement, leading to possible incorrect compensations to be made for scattered X-rays and occurrence of artifacts Aa–Ac.

Figure 16:
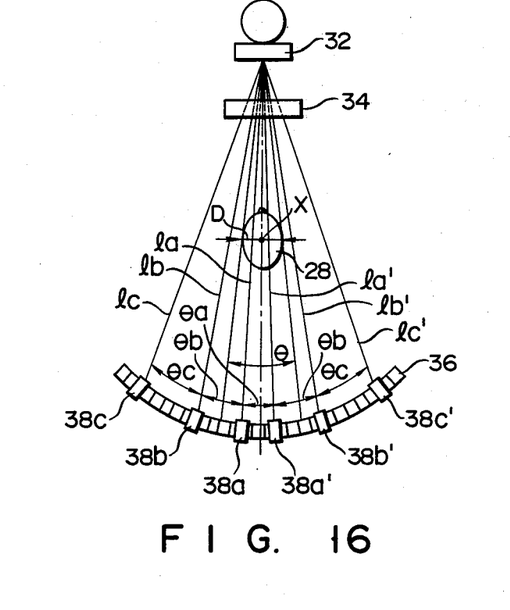
FIG. 16 is a front view of a third embodiment of the computed tomograph apparatus according to the present invention.

FIG. 16 shows a third embodiment of the present invention. In this embodiment, a plurality of scattered ray detectors 38a–38c and 38a'–38c' are provided symmetrically to slice plane Y in such a manner that scattered ray detectors 38a, 38b, and 38c are located further from the slice plane in descending order, and that the mutual relationship of angles $\theta_c$, $\theta_b$, and $\theta_a$, formed by lines $l_c$ and $l_b$, $l_b$ and $l_a$, $l_a$ and $l_a'$ connecting X-ray tube 32 and detectors 38a–38c and 38a'–38c', are expressed as $\theta_a < \theta_b < \theta_c$. Because of the symmetrical arrangement of the scattered ray detectors, the angles formed by lines $l_c'$ and $l_b'$ and $l_b'$ and $l_a'$ are identical to angles $\theta_c$ and $\theta_b$, respectively.

Figure 17:
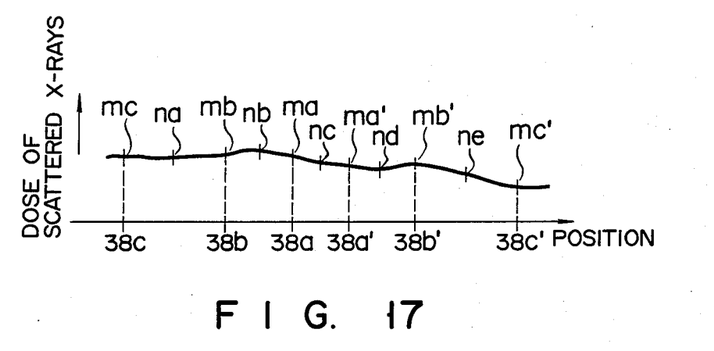
FIG. 17 is a graphical illustration of the characteristics of the apparatus shown in FIG. 16.

FIG. 17 shows a distribution of scattered ray doses detected when a scanning operation is conducted by rotating X-ray tube 32, collimator 34, principal detector 36 and scattered ray detectors 38a–38c and 38a'–38c' integrally around the axis of rotation X. Since the values of X-ray does $m_a$–$m_b$ and $m_a'$–$m_c'$ for the positions, where scattered ray detectors 38a–38c and 38a'–38c' are respectively located, are actually measured values, the accuracy level of scattered ray detection of this apparatus is high. Values $n_a$–$n_e$ for so many positions located between adjacent detectors are deterimined by interpolation.

It will be appreciated that the computed tomograph apparatus of FIG. 16 can compensate the effects of scattered rays at an enhanced level of accuracy even when the subject of examination is relatively small, and a pair of scattered ray detectors 38a and 38a' are positioned within angle $\theta$ determined by the width of the subject. In other words, a highly reliable compensation can be made by using the X-ray doses values which are actually detected and measured by the pair of scattered ray detectors 38a and 38a'.

Figure 18:
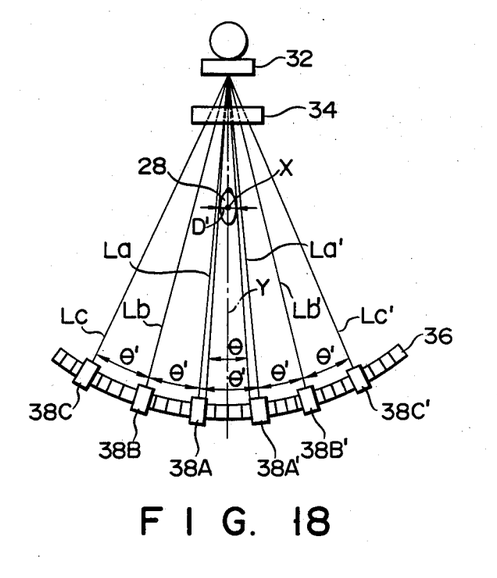
FIG. 18 is an alternative arrangement of the scattered ray detectors of the apparatus shown in FIG. 16.

FIG. 18 shows an alternative configuration of the above described third embodiment of the present invention. The advantages of the third embodiment may be easily understood by referring to this alternative. In this alternative, a plurality of scattered ray detectors 38A–38C and 38A'–38C' are provided symmetrically to slice plane Y in such a manner that the angles formed by pairs of lines Lc and Lb, Lb and La and La and La', connecting X-ray tube 32 to scattered ray detectors 38A–38C and 38A'–38C', are equal to one another, which are commonly denoted by $\theta'$.

Figure 19:
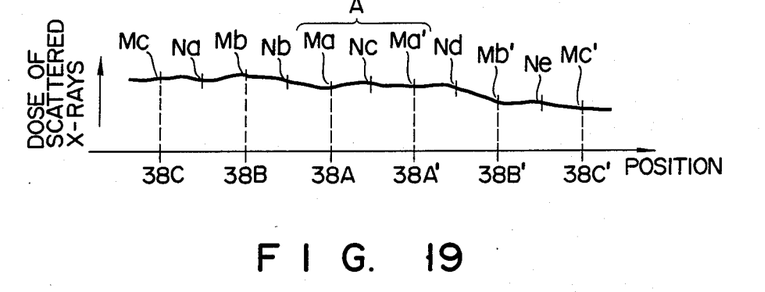
FIG. 19 is a graph showing the characteristics of the scattered ray detectors arranged as is shown in FIG. 18.

FIG. 19 shows the distribution of scattered ray doses detected by the scattered ray detectors when X-ray tube 32, principal detector 36 and scattered ray detectors 38A–38C and 38A'–38C' are integrally rotated around axis X of rotation. Since X-ray doses Ma–Mc and Ma'–Mc' for the positions, where scattered ray detectors 38A–38C and 38A'–38C' are respectively located, are actually measured values, the accuracy level of scattered ray detection of this alternative apparatus is high. Values Na–Ne for so many positions located between adjacent detectors are determined by interpolation.

An apparatus having the configuration described above cannot compensate for the effect of scattered rays when the width of the subject is relatively small. To provide a tomogram of subject 28 having a width D' by means of this apparatus, scattered rays must compensated by using the interpolated value for the area A shown in FIG. 19 because any of scattered ray detectors 38A–38C and 38A'–38C' are not located within angle $\theta$ for the effective area for subject 28 having a width D' when the interpolated value for area A is used, the compensation accuracy will be inevitably low.

Figure 20:
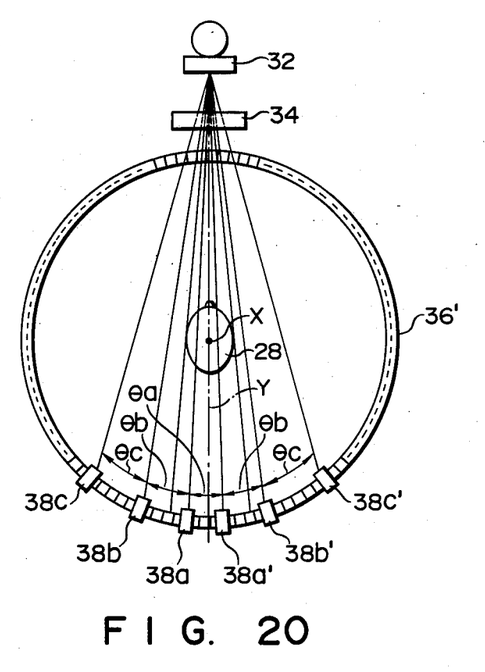
FIG. 20 is a front view of a so-called fourth generation computed tomograph apparatus to which the arrangement of the scattered ray detector as shown in FIG. 16 is applied.

FIG. 20 shows a so-called fourth generation computed tomograph apparatus, in which scattered ray detectors are arranged as is shown in FIG. 16. In this apparatus, principal detector 36' is ring-shaped, and covers subject 28 all around, and is rigidly secured in position as illustrated. X-ray tube 32, collimator 34, and scattered ray detectors 38a–38c and 38a'–38c' are integrally rotated around axis X of rotation, thereby scanning the subject. Scattered ray detectors 38a–38c and 38a'–38c' are arranged in the same manner as in the third embodiment. Hence, the apparatus of this type is as effective as the above embodiment in terms of accuracy of compensation of scattered rays.

It should be noted that some of scattered ray detectors 38a–38c and 38a'–38c' are located outside the area covered by sector angle $\theta$ of emission of X-rays because scattered rays are outside the area within sector angle $\theta$.

Figure 21:
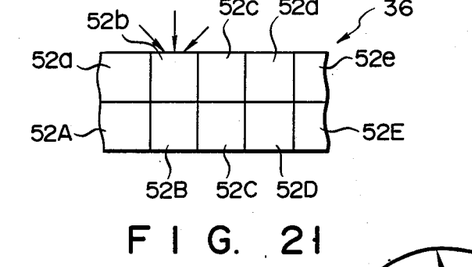
FIG. 21 is a schematic illustration of the principal detector used in a fourth embodiment of the computed tomograph apparatus according to the invention.
Figure 23:
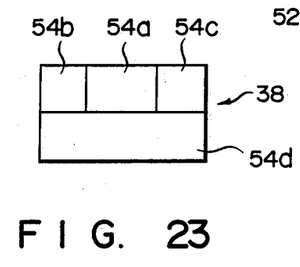
FIG. 23 is a schematic illustration of one of the scattered ray detectors used in the fourth embodiment.

FIGS. 21 and 23 schematically illustrate principal detector 36 and scattered ray detector 38, respectively, both of which are used in a fourth embodiment of the present invention.

Figure 22:
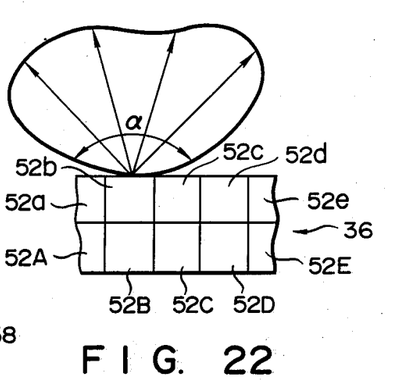
FIG. 22 is a schematic view of the principal detector shown in FIG. 21, illustrating its characteristics.

In the fourth embodiment, a scintillation detector, which is used as principal detector 36, comprises a plurality of scintillators 52a–52e and a plurality of photodiodes 52A–52E. Each of scintillator 52a–52e can detect a X-rays coming to it with any incident angle as shown in FIG. 21 for scintillator 52b. Scintillators 52a and 52c, which are adjacent to scintillator 52b as is shown in FIG. 21, act as screens to block X-rays passing through scintillator 52b. Thus the polar response characteristics of scintillator 52b for X-ray detection can be illustrated as shown in FIG. 22, along with effective incident angle $\alpha$. The polar response characteristics of the rest of the scintillators 52a, 52c, 52d and 52e are similar to those of scintillator 52b.

Scattered ray detector 38 is configured as shown in FIG. 23, where a scintillator 54a is sandwiched between two X-ray screening members 54b and 54c to form a layer placed on a layer of photodiode 54d. X-ray screening members 54b and 54c located to the both sides of scintillator 54a are typically made of lead (Pb), molybdenum (Mo) or tungsten (W).

Figure 24:
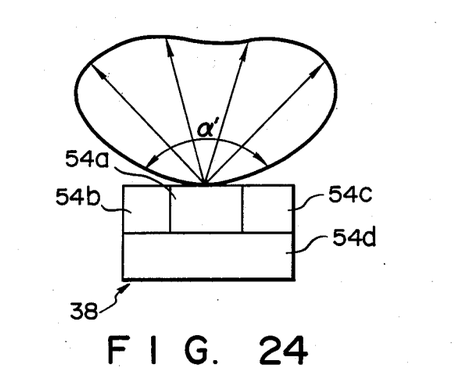
FIG. 24 is a schematic view of the scattered ray detector as shown in FIG. 23, illustrating its characteristics.

Scattered ray detector 38 typically has polar response characteristics with effective incident angle $\alpha'$ as is shown in FIG. 24 because of X-ray screen members 54b and 54c located on the both sides of scintillator 54a. Its effective incident angle $\alpha'$ can be made very close to that of principal detector 36 by the use of a pair of screen members 54b and 54c. If so, the X-ray detection characteristics of scattered ray detector 38 can be also very close to that of principal detector 36, and can minimize occurrence of artifacts.

Figure 25:
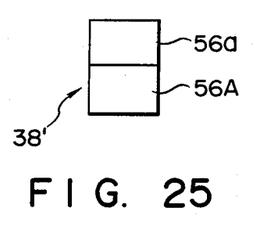
FIG. 25 is a schematic illustration of a scattered ray detector that can be alternatively used for the one shown in FIG. 23.
Figure 26:
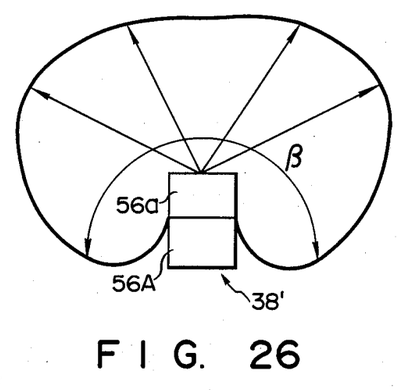
FIG. 26 is a schematic view of the scattered ray detector as shown in FIG. 25, illustrating its characteristics.

FIG. 25 is a schematic illustration of an alternative scattered ray detector. This alternative scattered ray detector 38 is, in fact, a scintillation detector, and has the characteristics which are specific to a scintillator. (It is a single channel detector comprising a scintillator 56a and a photodiode 56A.) Therefore, as shown in FIG. 26, the polar response characteristics of this scattered ray detector 38' has an effective incident angle which is considerably greater than effective incident angle $\alpha$ of principal detector 36. Thus, principal detector 36, and this alternative scattered ray detector 38' have respective polar response characteristics which are significantly different from each other. Detectors 36 and 38' inevitably allow artifacts to occur, though they are composed of the scintillation detectors of the same type.

Figure 27:
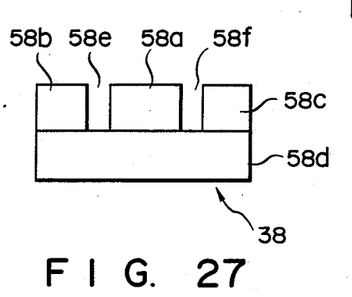
FIG. 27 shows a first modification of the scattered ray detector shown in FIG. 23.

FIG. 27 shows a first modification of the scattered ray detector of FIG. 23. In this modified detector 38, spaces 58e and 58f are provided between scintillator 58a and X-ray screen member 58b, and between scintillator 58a and X-ray screen member 58c, respectively, which are collectively placed on the layer of photo-diode 58d. The detector of this design has the advantage that its polar response characteristics can be selectively changed by altering the dimensions of spaces 58e and 58f.

Figure 28:
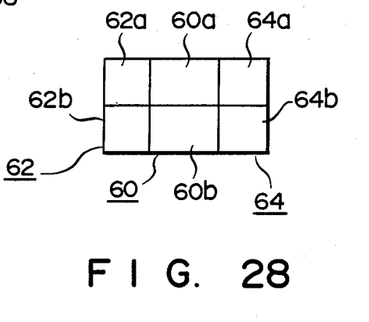
FIG. 28 shows a second modification of the scattered ray detector shown in FIG. 23.

FIG. 28 shows a second modification of the scattered ray detector of FIG. 23. In this modified scattered ray detector 38, second and third scintillation detectors 62 and 64 are provided, one on each side of the first scintillation detector 60. Scintillation detectors 60, 62 and 64 respectively comprise scintillators 60a, 62a and 64a, and photodiodes 60b, 62b and 64b. An output line (not shown) is connected to the first scintillation detector 60, and output detection signals are supplied from the first scintillation detector 60 by way of the output line. No output lines are connected to second scintillation detector 62 or third scintillation detector 64 since these scintillation detectors are used in great numbers, as X-ray screen members. The scattered ray detector of this design has the advantage that it can be made of a scintillation detector 60 and two X-ray screen members 62 and 64, which are identical, significantly simplifying the process of manufacturing of scattered ray detectors.

Principal detectors 36 and scattered ray detectors 38 used in the fourth embodiment can be applied to a computed tomograph apparatus of the fourth or the fifth generation which is characterized by detectors rigidly fixed around a subject and a smaller number of movable components. Materials that can be used as X-ray screen members are not limited to those cited above and any materials can be adequately applied so long as they can effectively shield X-rays.

What is claimed is:

1. A computed tomograph apparatus for obtaining tomograms of a subject under examination, comprising:
   a supporting table for supporting said subject, and on which a tomogram image pick-up area is defined;
   an X-ray source for radiating X-rays onto said image pick-up area, said X-rays proceeding along a slice plane which intersects with said image pick-up area;
   a principal detector provided in said slice plane, for detecting X-rays transmitted linearly through said subject placed in said image pick-up area; and
   a scattered ray detector provided in an arc existing in a plane perpendicular to said slice plane, for detecting scatter X-ray radiation not transmitted linearly through said subject, said arc having its center in said slice plane and a radius which is equal to the distance between said center and said principal detector.

2. The computed tomograph apparatus according to claim 1, wherein the center of said arc is within said image pick-up area.

3. The computed tomograph apparatus according to claim 1, further comprising a means for rotating said X-ray source and optionally said principal detector and/or said scattered ray detectors, around an axis of rotation within said image pick-up area.

4. The computed tomograph apparatus according to claim 3, wherein the center of said arc is in said image pick-up area located farther from said X-ray source than a plane containing said axis of rotation and perpendicular to a line passing said X-ray source and said axis of rotation.

5. The computed tomograph apparatus according to claim 3, further comprising a cylindrical protective housing situated nearer to said image pick-up area than said principal detector and said scattered ray detectors, for surrounding and protecting said subject under examination, said housing having a first opening, for admitting X-rays emitted from said X-ray source into said image pick-up area, and a second opening, for introducing X-rays transmitted through said subject in said image pick-up area, and other X-rays, to said principal detector and said scattered ray detectors.

6. The computed tomograph apparatus according to claim 5, wherein said second opening is formed having such dimensions that at least X-rays proceeding linearly from the intersection of said slice plane and said axis of rotation, toward said principal detector and said scattered ray detectors, can pass therethrough.

7. The computed tomograph apparatus according to claim 1, wherein the distance between said scattered ray detector and said slice plane is shorter than or equal to the distance between said image pick-up area and said principal detector.

8. The computed tomogram apparatus according to claim 3, further comprising additional scattered ray detectors.

9. The computed tomograph apparatus according to claim 8, wherein the distance between said axis of rotation and a line connecting each of said scattered ray detectors and said X-ray source is different from the distance between said axis of rotation and a line connecting any other scattered ray detector and said X-ray source.

10. The computed tomograph apparatus according to claim 8, wherein said scattered ray detectors are arranged such that, for each scattered ray detector, the angle defined by the line connecting said X-ray source and each scattered ray detector and the line connecting the X-ray source and a first adjacent scattered ray detector is greater than the angle defined by the line connecting the x-ray source and each scattered ray detector and the line connecting the X-ray source and a second adjacent scattered ray detector located nearer to a plane which contains said axis of rotation and in which said X-ray source exists than said first adjacent scattered ray detector.

11. The computed tomograph apparatus according to claim 1, wherein said scattered ray detector comprises a detection member for detecting X-rays, conversion means for converting X-rays into an electric signal in accordance with the intensity of those X-rays, and a pair of X-ray screen members, one provided at each side of said detection member.

12. The computed tomograph apparatus according to claim 11, wherein said detector member and said X-ray screen members are arranged in contact with each other.

13. The computed tomograph apparatus according to claim 11, wherein a space is provided between said detection member and each of said X-ray screen members.

14. A computed tomograph apparatus for obtaining tomogram images of a subject under examination, comprising
a supporting table for supporting said subject, and on which a tomogram image pick-up area is defined,
an X-ray source for radiating X-rays onto said image pick-up area, said X-rays proceeding along a slice plane intersecting with said image pick-up area and said source having an axis of rotation,
a principal detector provided within said slice plane for detecting X-rays transmitted linearly through said subject placed in said image pick-up area,
a plurality of scattered ray detectors for detecting X-rays scattered within said subject, each of said scattered ray detectors being arranged at a different distance from said axis of rotation in a direction parallel to the slice plane, said scattered ray detectors not contacting each other, and
a driving means for rotating said X-ray source and optionally said principal detector and/or said scattered ray detectors, around the axis of rotation within said image pick-up area, the distance between said axis of rotation and a line connecting each of said scattered ray detectors and said X-ray source being different from the distance between said axis of rotation and a line connecting any other scattered ray detector and said X-ray source.

15. The computed tomograph apparatus according to claim 14, wherein each of said scattered ray detectors includes a detection member for detecting X-rays, and a pair of X-ray screen members, one provided on each side of said detection member.

16. A computed tomograph apparatus for obtaining tomograms of a subject under examination, comprising
a supporting table for supporting said subject, and on which a tomogram image pick-up area is defined,
an X-ray source for radiating X-rays onto said image pick-up area, said X-rays proceeding along a slice plane intersecting with said image pick-up area,
a principal detector provided within said slice plane, for detecting X-rays transmitted linearly through said subject placed in said image pick-up area, and
a plurality of scattered ray detectors for detecting X-rays scattered within said subject, said scattered ray detectors being arranged at a predetermined spacing in a direction parallel to the slice plane, said scattered X-ray detectors not contacting each other, said scattered ray detectors being arranged such that the angle defined by the line connecting said X-ray source and each scattered ray detector and the line connecting the X-ray source and a first adjacent scattered ray detector is greater than the angle defined by the line connecting the X-ray source and each scattered ray detector and the line connecting the X-ray source and a second adjacent scattered ray detector located nearer to a plane which contains said axis of rotation and in which said X-ray source exists than said first adjacent scattered ray detector.

17. The computed tomograph apparatus according to claim 16, wherein each of said scattered ray detectors includes a detection member for detecting X-rays, and a pair of X-ray screen members, one provided on each side of said detection member.

* * * * *